US007402805B1

(12) United States Patent
Savoie et al.

(10) Patent No.: US 7,402,805 B1
(45) Date of Patent: Jul. 22, 2008

(54) DEVICE FOR THE IN-SITU MEASUREMENT OF ACOUSTICALLY STIMULATED BIOLUMINESCENCE

(75) Inventors: Matthew J. Savoie, Mansfield, MA (US); Michael J. Forbes, Hanover, ME (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 131 days.

(21) Appl. No.: 11/208,126

(22) Filed: Aug. 22, 2005

(51) Int. Cl.
*G01T 1/10* (2006.01)
*G01T 1/20* (2006.01)
*C12M 1/34* (2006.01)
*C12M 3/00* (2006.01)
*C12N 13/00* (2006.01)

(52) U.S. Cl. ............................ 250/361 C; 435/288.7; 435/808; 435/286.7; 435/173.1; 422/82.05; 422/82.09; 422/52; 356/28; 356/427

(58) Field of Classification Search ............. 250/361 C; 435/288.7, 808, 286.7, 173.1; 422/82.05, 422/82.09, 52; 356/28, 427
See application file for complete search history.

(56) References Cited

U.S. PATENT DOCUMENTS 4,978,854 A * 12/1990 Lapota et al. ........... 250/361 C
5,061,445 A 10/1991 Zoski et al.
5,264,906 A 11/1993 Ferer et al.
5,840,572 A 11/1998 Copeland et al.
2006/0061225 A1* 3/2006 Beck et al. .................. 310/120

* cited by examiner

*Primary Examiner*—William H. Beisner
*Assistant Examiner*—Nathan A Bowers
(74) *Attorney, Agent, or Firm*—James M. Kasischke; Michael P. Stanley; Jean-Paul A. Nasser

(57) ABSTRACT

A device and method of use for measurement of in-situ bioluminescence generally comprising an acoustical pulse generator, a detector chamber, a lens assembly and a photomultiplier tube. The generator comprises transducers which can generate acoustical energy in the object field of the device. The acoustical energy provides a stimulus of aquatic organisms within the object field (typically an aqueous volume) to produce the bioluminescence. The generator is positioned outside of the detector chamber and the photomultiplier tube and lens assembly are mounted within the chamber. The lens assembly restricts light to the photomultiplier tube of that bioluminescence light originating only from the volume. The photomultiplier tube detects the bioluminescence generated by any aquatic organisms in a captured volume or if a changing measurement occurs by water flow in the volume. The output of the photomultiplier tube is provided to a controller to be analyzed.

3 Claims, 1 Drawing Sheet

DEVICE FOR THE IN-SITU MEASUREMENT OF ACOUSTICALLY STIMULATED BIOLUMINESCENCE

STATEMENT OF GOVERNMENT INTEREST

The invention described herein may be manufactured and used by or for the Government of the United States of America for governmental purposes without the payment of any royalties thereon or therefore.

BACKGROUND OF THE INVENTION (1) Field of the Invention

The present invention relates to the field of detecting bioluminescent emissions and more particularly to a bioluminescence detection device in which a voltage wave train is supplied to one or more of a plurality of transducers of an acoustical pulse generation system. The transducer generates acoustical energy thereby stimulating aquatic organisms to bioluminescence in the object field of an optical system which in turn records the number of photons received for the duration of the acoustical stimulus.

(2) Description of the Prior Art

Bioluminescence is a visible light produced either intermittingly or continuously by numerous aquatic organisms. Many marine dinoflagellate species are able to produce bioluminescence as part of their daily physiological processes. Similarily, some marine bacteria are also bioluminescent. Since various toxicants are known to reduce the light intensity output of bioluminescent bacterial cultures, the bacteria have been used as test organisms to detect the toxicity of atmospheric samples, herbicides and some chemicals.

In order to effectively detect bioluminescence, various optical instrumentation has been developed to provide data which can correlate with organism distribution patterns. Instrumentation which measures stimulated bioluminescence provides a substantial utility for rapid profiling of aquatic organisms.

In Copeland et al. (U.S. Pat. No. 5,840,572), a system for measuring the toxicity levels of a solution is disclosed. In the cited reference, a stress generator in a sample container generates pressure pulses which stimulate an organism to generate measurable light emissions. A light detection system generates an electric pulse in response to each detected light emission. A controller enables the stress generating system and the light detection system, and then counts the electric pulses within a predetermined period of time in order to produce measurable points for toxicity.

An improvement to the known art of acoustically stimulating bioluminescent organisms is providing a bioluminescence detection device in which the detection device may be fielded in-situ (where the sample volume is in the open ocean) by which water can flow freely through a volume thus allowing for measurement of a continuously changing sample. Using acoustic generation would stimulate bioluminescent organisms without damaging the organisms and would allow a consistent stimulus. By allowing for in-situ measurement, a more realistic observation of the behavior of bioluminescent organisms is attainable than by the use of present controlled and enclosed measurement devices.

SUMMARY OF THE INVENTION

It is therefore a general purpose and object of the present invention to provide a bioluminescence detection device in which the detection device may be fielded in-situ by which water can flow freely through a volume thus allowing for measurement of a continuously changing sample of organisms which are unaffected by a non-natural environment.

It is a further object of the present invention to provide a bioluminescence device in which bioluminescent organisms may be stimulated without the impact of man-made containment structures.

It is a still further object of the present invention to provide a bioluminescence detection device in which bioluminescent organisms may be stimulated without being damaged.

It is a still further object of the present invention to provide a bioluminescence detection device in which bioluminescent organisms may be stimulated consistently.

In order to attain the objects described above, there is provided a device for bioluminescence measurement generally comprising an acoustical pulse generator, a tubular detector chamber, a lens assembly and a photomultiplier tube.

The acoustic pulse generator comprises acoustic transducers which can project a high-powered narrow beam operation. The transducers are operated by supplying a voltage wave train to one or a plurality of the transducers which in turn generates acoustical energy in the object field of the device. The generated acoustical energy provides a stimulus or agitation of any aquatic organisms within the object field (typically an aqueous volume). The stimulated aquatic organisms produce the bioluminescence for measurement. The positioning of the transducers can also allow a stationary bioluminescence measurement if a volume is captured in addition to a measurement of the changing flow of water in the volume.

The lens assembly restricts a measurement of light to the photomultiplier tube of that light originating only from the volume of primary acoustic stimulation. The photomultiplier tube detects the bioluminescence generated by any aquatic organisms in a captured volume or if a changing measurement occurs by water flow in the volume. The output of the photomultiplier tube is provided in photons/sec in which the output can be further analyzed by a controller or any other receiver known to those skilled in the art.

The photomultiplier tube and lens assembly are mounted within the tubular detector chamber. A transparent optical window is positioned in one end of the tubular detector chamber and is mounted in alignment with both the photomultiplier tube and the lens assembly.

The acoustic transducers are mounted directly on the tubular detector chamber or can be additionally supported by a stainless steel tubular ring. In either configuration, the acoustic transducers can be adjusted and positioned so that the main acoustic axis is directed into the center of a bioluminescence measurement volume.

The device of the present invention allows the flexible positioning of the acoustic pulse generator by the transducers and is capable of measuring a stationary bioluminescence if a volume is captured or a changing bioluminescence if the volume is part of a free flow of water moving past the device.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawing wherein.

DESCRIPTION OF THE PREFERRED EMBODIMENT

Figure 1:
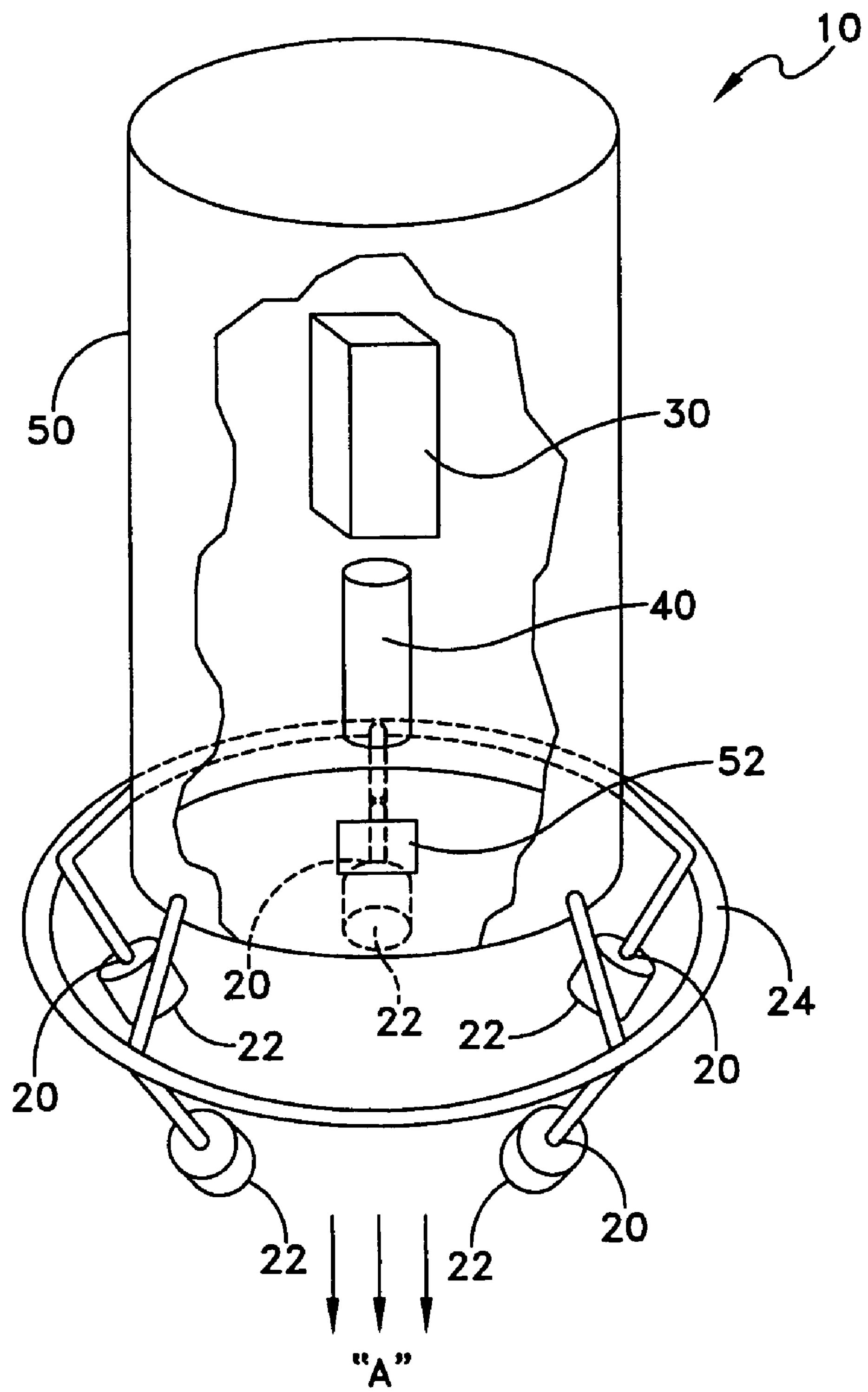
FIG. 1 shows a diagram of the in-situ bioluminescence measurement device of the present invention.

Referring now to FIG. 1, there is shown a bioluminescence measurement device 10 of the present invention generally comprising an acoustical pulse generator 20, photomultiplier tube (PMT) 30, a lens assembly 40 and a tubular detector chamber 50.

The acoustic pulse generator 20 preferably comprises five acoustic transducers 22, known to those skilled in the art, in which the transducers can project a high-powered narrow beam operation. The transducers 22 are operated by supplying a voltage wave train to one or a plurality of the transducers which in turn generates acoustical energy in the object field (as indicated by a volume surrounding and part of a flow in direction "A") of the bioluminescence measurement device 10. The generated acoustical energy provides a stimulus or agitation of any aquatic organisms within the object field. The stimulated aquatic organisms produce the bioluminescence. The positioning of the transducers 22 can also allow a stationary bioluminescence measurement if a volume is captured.

The photomultiplier tube 30 and lens assembly 40 are mounted within the tubular detector chamber 50. The lens assembly 40 restricts a measurement of light to the photomultiplier tube 30 of that light originating only from the volume of primary acoustic stimulation. The photomultiplier tube 30 detects the bioluminescence generated by any aquatic organisms in a captured volume or if a changing measurement occurs by flow in the direction "A" in the volume. The output of the photomultiplier tube 30 is provided in photons/sec in which the output can be further analyzed by a controller or any other receiver known to those skilled in the art.

A transparent optical window 52 is positioned in one end of the tubular detector chamber 50 and is mounted in alignment with both the photomultiplier tube 30 and the lens assembly 40 to allow measured bioluminescence to reach both. The tubular detector chamber 50 is preferably made of stainless steel thereby providing a durable of and light-tight chamber allowing operation to depths of up to 6000 feet.

The acoustic transducers 22 are mounted directly on the tubular detector chamber 50 or can be additionally supported by a stainless steel tubular ring 24. In either configuration, the acoustic transducers 22 can be adjusted and positioned so that the main acoustic axis is directed into the center of a bioluminescence measurement volume.

It is therefore a primary advantage of the bioluminescence measurement device 10 of the present invention that the device allows the flexible positioning of the acoustic pulse generator 20 by the transducers 22 and is capable of measuring a stationary bioluminescence if a volume is captured or a changing bioluminescence if the volume is part of a free flow of water moving past the device.

Thus, the several aforementioned objects and advantages of the present invention are most effectively attained. Although preferred embodiments of the invention have been disclosed and described in detail herein, it should be understood that this invention is in no sense limited thereby and its scope is to be determined by that of the appended claims.

What is claimed is:

1. A device for measuring bioluminescence of an aqueous volume, comprising:

a tubular detector chamber having a closed first end and a closed second end;

an optical window positioned within said second end with a face of said window interior to said tubular detector chamber and an opposite face of said window exterior to said tubular detector chamber and facing the aqueous volume;

an acoustic pulse generator mounted at said second end on an exterior of said tubular detector chamber, said acoustic pulse generator having a plurality of transducers wherein said pulses generated by at least one transducer is capable of stimulating aquatic organisms to bioluminescence within the aqueous volume;

a photomultiplier tube secured within the interior of said tubular detector chamber, said photomultiplier tube capable of measuring the bioluminescence generated by the aquatic organisms; and a lens assembly mounted with said photomultiplier tube and in alignment with said optical window, wherein said lens assembly is capable of restricting light from said optical window to said photomultiplier tube as the detection of bioluminescence from the aqueous volume to the measurement by said photomultiplier tube;

wherein said transducers are mechanically mounted to a ring affixed to an end of said tubular detector chamber such that said transducers extend away from said tubular detector chamber to encompass an area parallel to said ring wherein said transducers are adjustably positioned along said ring to generate an acoustic pulse at a specified section of the aqueous volume;

wherein said transducers are capable of generating an acoustic pulse to (a) an aqueous free flow thru the specified section and wherein said photomultiplier tube is capable of detecting the bioluminescence generated by the stimulated aquatic organisms in the free flow;

wherein said transducers are capable of generating an acoustic pulse thru the specified section and wherein said photomultiplier tube is capable of detecting the bioluminescence generated by the aquatic organisms in the specified section wherein the aqueous volume is static.

2. The device in accordance with claim 1 wherein an output of said photomultiplier tube is provided in photons per second.

3. The device in accordance with claim 2 wherein said ring and said tubular detector chamber are stainless steel.

* * * * *